United States Patent [19]

Vanderpool et al.

[11] Patent Number: 4,629,809

[45] Date of Patent: Dec. 16, 1986

[54] PROCESS FOR SELECTIVELY PREPARING ACETIC ACID BY CARBONYLATION OF METHANOL IN THE PRESENCE OF A NOVEL IODIDE-FREE CATALYST SYSTEM

[75] Inventors: Steven H. Vanderpool, New Braunfels; Jiang-Jen Lin, Round Rock; Roger G. Duranleau, Georgetown, all of Tex.

[73] Assignee: Texaco Inc., White Plains, N.Y.

[21] Appl. No.: 515,749

[22] Filed: Jul. 21, 1983

[51] Int. Cl.⁴ .................. C07C 51/12; C07C 53/08
[52] U.S. Cl. .................. 562/519; 260/413; 260/549; 560/232; 562/517; 568/698; 568/877
[58] Field of Search .................. 562/519, 517; 260/413

[56] References Cited

U.S. PATENT DOCUMENTS

| | | | |
|---|---|---|---|
| 3,855,307 | 12/1974 | Rony et al. | 562/519 |
| 4,356,126 | 10/1982 | Drent | 562/519 |
| 4,414,410 | 11/1983 | Lin et al. | 562/517 |

*Primary Examiner*—Vivian Garner
*Attorney, Agent, or Firm*—Jack H. Park; Kenneth R. Priem; Cynthia L. Kendrick

[57] ABSTRACT

A process for producing acetic acid is disclosed which comprises reacting methanol with carbon monoxide at an elevated temperature and pressure in the presence of an iodine-free catalyst system wherein the catalyst consists of ruthenium compound, quaternary phosphonium salt, cobalt-compound and inorganic acid or an organic acid, reacted in combination in a liquid form or a ruthenium on inert solid support catalyst with a sulfur-containing acid promoter.

1 Claim, No Drawings

PROCESS FOR SELECTIVELY PREPARING ACETIC ACID BY CARBONYLATION OF METHANOL IN THE PRESENCE OF A NOVEL IODIDE-FREE CATALYST SYSTEM

FIELD OF THE INVENTION

This invention pertains to the production of acetic acid with high selectivity by carbonylation of methanol in the presence of a novel iodide-free catalyst system at a temperature of at least 150° C. and a pressure of at least 500 psi.

BACKGROUND OF THE INVENTION

Although a wide variety of aliphatic carboxylic acids of differing carbon numbers and structures are presently important articles of commerce, production of acetic acid is especially desirable. Important applications for this acid include the production of cellulose acetate and vinyl acetate. There are several commercially proven routes to acetic acid manufacture, including oxidation of ethylene via acetaldehyde, liquid-phase oxidation of saturated hydrocarbons, n-butane oxidation and methanol carbonylation. To the extent that methanol is currently produced from synthesis gas (a mixture of carbon monoxide and hydrogen), acetic acid via methanol carbonylation also effectively becomes a 'syngas' chemical. Furthermore, since syngas may be generated from a variety of sources, including heavy oil residuals and coal stocks, this syngas route to acetic acid will likely become increasingly important. (See: "Trends in Petrochemical Technology" by A. M. Brownstein (1976), Chapters 4 and 5; and "Petrochemicals from Coal" by P. M. Spitz, Chemtech, May 1977, p. 295.

Carbonylation processes for the preparation of carboxylic acids from alcohols are well known in the art. These have been directed especially to the production of acetic acid by the carbonylation of methanol. In particular, a variety of soluble and supported forms of cobalt, nickel, iron, iridium and rhodium have been patented as catalysts for methanol carbonylation to acetic acid. In the case of carbonylation processes of the prior art, comprising processes employing metal carbonyls or modified metal carbonyls of cobalt, iron and nickel, each is characterized by the need for high partial pressures of carbon monoxide in order that the carbonyls remain stable under the 200° C. temperatures normally employed. See: "Carbon Monoxide in Organic Synthesis" by J. Falbe (1976), Chapters II and III. Dicobalt octacarbonyl, for example, requires partial pressures of carbon monoxide in the 4,000 psi to 10,000 psi range. Furthermore, said cobalt, nickel and iron catalysts of the prior art generally display relatively poor selectivities to the desired carboxylic acids due to the substantial formation of undesirable by-products. Said by-products comprise substantial amounts of ethers, aldehydes, higher carboxylic acids, carbon dioxide, methane and water. See: N. Von Kutepow, et al., Chemie-Ing. Techn. 37,383 (1965).

A series of very active carbonylation catalysts have been patented. See for example: Belgium Pat. No. 713,296 (1968), U.S. Pat. No. 3,772,380 (1973) and U.S. Pat. No. 3,717,670 (1973), where the active constituents contain a rhodium or iridium component in combination with a halogen promoter. These catalyst combinations are characterized by being effective under relatively mild operating conditions and achieving high selectivity to desired acetic acid in the case of methanol carbonylation. However, both iridium and rhodium are rare, costly metals, and rhodium in particular is predicted to be in increasingly short supply due to expanded uses in petrochemical catalysis and in catalytic muffler applications. Furthermore, in recent reports, it is noted that much dimethylether is also formed during the rhodium-catalyzed carbonylation of methanol in pure methanol solvent. See: T. Matsumato et al., Bull. Chem. Soc. Japan, 50, 2337 (1977).

Roth et al. describes a homogeneous liquid phase catalyst which is capable of bringing about methanol carbonylation at 1 atm in 99% selectivity using a rhodium compound, an iodide promoter and a solvent. Although this system is very effective for producing acetic acid, the corrosive iodine promoter is still present and rhodium is expensive. See: Roth, J. F. et al Chem. Technol. 600, October (1971).

In a discussion of the art of carbonylation of methanol to acetic acid, Forster attempts to define various rhodium species present in the catalytic cycle when rhodium(III) halide in particular is charged to the reaction as the catalyst precursor. In his model he presents a pathway for the reaction which is consistent with the observed independence of the overall reaction rate of carbon monoxide pressure and methanol concentration. See: Forster, D. JACS 98 846 (1976).

An article in J. of Catalysis 47 269, (1977), enumerates the disadvantages of the best known methanol carbonylation reactions in that the reactors, separators and recycle loops must be constructed of expensive corrosion-resistant materials and that recovery of the catalyst and promoter from the reaction products requires several separators because of the relatively high volatility of the iodide compounds. In this article an attempt is made to identify a suitable promoter substitute for idodide. Promoters chosen were pentafluoro and pentachlorobenzenethiol; however, the effectiveness of these promoters is much less than with iodide. For example, the rate of methanol carbonylation is about 4% of the rate with methyl iodide at a comparable temperature.

U.K. Patent application GB No. 2007212A by Isshiki and Kijima discloses a method of producing carboxylic acids by reacting alcohols with carbon monoxide in the presence of elemental nickel or a nickel compound, an organic compound of a trivalent nitrogen-group element, and iodine or an iodine compound. The asserted advantage of this system is the use of milder conditions and an inexpensive catalyst, but iodine is still necessary.

In U.S. Pat. No. 3,856,856, Nozaki discloses the use of a platinum promoter in a cobalt-iodide catalyst system. Here, the yield of methyl acetate is generally higher than that of acetic acid.

In U.K. Patent application GB No. 2007658A, Isshiki and Kijima disclose a method for reacting an alcohol with carbon monoxide to produce an aliphatic carboxylic acid using a Group VIII compound and at least one iodine-containing compound as a promoter, optionally in the presence of a trivalent nitrogen-group element as an accelerating agent, and a solvent.

In U.S. Pat. No. 3,769,324, to Paulik et al. a process is disclosed for the preparation of aromatic carboxylic acids and esters in the presence of a catalyst system including a metal selected from the group consisting of iridium, osmium and ruthenium and a halogen component.

The various catalyst systems of the prior art all have distinct disadvantages. Either selectivities are not very high, extremely high pressures are necessary, expensive and increasingly hard to find metal catalysts are used, or, the most prevalent disadvantage is the need to use an iodide promoter which is corrosive and results in added expense in constructing and maintaining reactors, separators and recycle loops. Although the system devised by Roth et al. is very effective, the use of iodine is a major disadvantage.

Initial attempts to devise carbonylation catalyst systems which use promoters other than iodide have been unsuccessful or have resulted in systems with very poor conversion and selectivity.

As will be discussed, it is an object of this invention to design a catalyst system for carbonylation of methanol to acetic acid which uses mild conditions including mild pressures, does not use expensive rhodium, does not use a corrosive iodide promoter and which has selectivities high enough for commercial consideration.

SUMMARY OF THE INVENTION

These and other objects are achieved by the process of this invention comprising preparing acetic acid by carbonylation of methanol at a temperature of at least 150° C. and a pressure of at least 500 psi in the presence of a catalyst system consisting of:
(a) a catalyst containing a ruthenium-containing compound, a quaternary phosphonium salt, a cobalt-containing compound and an inorganic or an organic acid.
(b) a ruthenium on carbon catalyst with a sulfur-containing acid as a promoter.

DETAILED DESCRIPTION OF THE INVENTION

In the broadest aspect of this invention acetic acid is prepared from methanol by contacting said reactant with carbon monoxide in the presence of an iodine free novel soluble or solid catalyst system essentially comprising a ruthenium-containing compound, a quaternary phosphonium salt, a cobalt-containing compound, an inorganic acid in the soluble form and in the solid form a carbon support wherein a sulfur-containing acid is the promoter, and heating said reaction mixture at a temperature of at least 150° C. under superatmospheric pressures until the desired acid products are formed. The overall reaction may be illustrated by the following equation I:

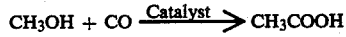

In the narrower practice of this invention, acetic acid is prepared from methanol by a process comprising the following steps:
(a) Contacting said methanol with a soluble or solid catalyst comprising a ruthenium-containing compound, a cobalt-containing compound, a quaternary phosphonium salt or base and an inorganic acid and a supported ruthenium on carbon catalyst, wherein a sulfur-containing acid is used as a promoter;
(b) Heating said reaction mixture under super-atmospheric pressures of 500 psi or greater with sufficient carbon monoxide to satisfy the stoichiometry of the desired carboxylic acid or ester product, until substantial formation of the desired acids and the esters has been achieved, and
(c) Isolating said acids and the ester derivatives contained therein.

The soluble form of the iodide-free catalyst system for carbonylation of methanol and carbon monoxide to acetic acid essentially comprises:
a ruthenium-containing compound, a quaternary phosphonium salt, a cobalt-containing compound and an inorganic acid.

The solid form of the iodide-free catalyst system for carbonylation of methanol and carbon monoxide to acetic acid essentially comprises a ruthenium on carbon catalyst wherein a sulfur-containing acid is used as a promoter.

In order to present the inventive concept in the greatest possible detail as to promote its understanding, the following supplementary disclosure is submitted.

A. Catalyst Composition

The catalyst precursors that are suitable in the practice of this invention essentially include a ruthenium component, a cobalt component, a quaternary phosphonium salt or base and an inorganic acid or an organic acid or, alternately, a ruthenium on carbon catalyst wherein the promoter is a sulfur-containing acid. A wide range of ruthenium catalyst compositions may be employed.

B. Ruthenium Catalyst Component

In the catalyst of this invention, the ruthenium component may be in solution or dispersed on one or more solid carriers or supports. Where ruthenium is dispersed on a support, suitable supports for the ruthenium may include, but are not limited to, activated and inactivated carbons.

The supports may be in the form of powders, pellets, spheres, shapes and extrudates. They should also be of suitable porosity such that they may be employed in fixed or fluidized bed ratios.

The ruthenium component to be used in conjunction with other catalyst components either in soluble form as in the first embodiment of the invention, or for impregnating the solid support may be added in the form of a ruthenium oxide, as in the case of, for example, ruthenium(IV) dioxide, hydrate, anhydrous ruthenium(IV) dioxide and ruthenium(VIII) tetraoxide, or as the salt of a mineral acid, as in the case of ruthenium(II) chloride, hydrate, ruthenium(III) bromide, anhydrous ruthenium(II) chloride and ruthenium nitrate. Alternatively, the ruthenium may be added as the salt of a suitable organic carboxylic acid. Here examples include ruthenium(III) acetate, ruthenium(III) propionate, ruthenium hexafluoroacetylacetonate, ruthenium(III) trifluoroacetate, ruthenium octanoate, ruthenium naphthenate, ruthenium valerate and ruthenium(III) acetylacetonate. This invention also contemplates the use of carbonyl or hydrocarbonyl derivatives such as triruthenium dodecacarbonyl, $H_2Ru_4(CO)_{13}$ and $H_4Ru_4(CO)_{12}$, and substituted carbonyl species such as the tricarbonylruthenium(II) dimer, $[Ru(CO)_3Cl_2]_2$.

Ruthenium compounds, especially useful in the soluble form of the catalyst include triruthenium dodecacarbonyl, ruthenium(III) chloride, ruthenium oxide hydrate and ruthenium(III) acetate. The preferred compound is ruthenium oxide hydrate.

Effective ruthenium-containing compounds for use in impregnating the solid support to obtain a 1% ruthenium on carbon support include triruthenium dodecacarbonyl and ruthenium(III) acetate. Preferred is triruthenium dodecacarbonyl.

Generally, where the 1% ruthenium on carbon catalyst is to be used the solid phase of said ruthenium-containing catalyst system is prepared by first dissolving or slurrying the selected ruthenium carbonyl, ruthenium oxide, salt etc., e.g., RuCl$_3$.3H$_2$O, with a suitable solvent system and subsequently impregnating the selected inert support or carrier with said ruthenium-containing mixture. These solutions or slurries may be poured onto the carrier, or the solid carrier may be immersed in excess of the liquid solution or slurries, with the excess being subsequently removed.

The impregnated support is then maintained at a temperature sufficient to volatize the solvent component, e.g. at a temperature between 150° C. and 325° C., to permit drying of the composite solid catalyst. A vacuum may also be applied to the catalyst in order to volatalize the solvent, although use of vacuum is not essential. During this stage of the process, the volatile solvent evaporates from the solid catalytic product, and the ruthenium component remains on the support. Optionally this ruthenium impregnated solid may be treated with hydrogen or carbon monoxide/hydrogen mixtures at elevated temperatures in order to cause at least partial reduction of the ruthenium component to ruthenium metal or a low valency form of ruthenium such as ruthenium(I).

The solvent which may be used to dissolve the ruthenium oxide or salt compound prior to impregnation onto the support should be a liquid of relatively low boiling point (<150° C.). A preferable group of solvents include mineral acid solutions such as hydrochloric acid and nitric acid, carboxylic acids such as acetic acid, propionic acid, and halogenated solvents like chloroform and carbon tetrachloride, ketones such as acetone and methyl isobutyl ketone, alcohols such as methanol, isopropanol and tertbutanol, aromatics such as benzene, toluene and xylene, as well as certain heterocyclic solvents like pyridine and N-methylpyrrolidone. The choice of solvent is dependent optionally upon the nature of the ruthenium oxide or salt to be used for impregnation.

Generally it is believed, without limiting the invention thereby, that the catalytically active ruthenium species of this invention, during the alcohol carbonylation is in the form of a coordination complex of ruthenium and solid supports that may or may not, contain carbon monoxide ligands. Other moieties may also be present as desired, and the ruthenium may be introduced into the reaction zone as a coordination complex of ruthenium containing hydrido-ruthenium carbonyl.

C. Cobalt Catalyst Component

As previously pointed out in the process of this invention for producing acetic acid the reaction is conducted in the presence of a catalyst which, when not on a support, includes a cobalt-containing compound. The cobalt-containing compound employed may be a cobalt carbonyl or a compound capable of forming a cobalt carbonyl under reaction conditions.

The cobalt-containing catalyst precursors may take many different forms. For instance, the cobalt may be added to the reaction mixture in an oxide form, as in the case of, for example, cobalt(II) oxide (CoO) or cobalt(II, III) oxide (Co$_3$O$_4$). Alternatively, it may be added as the salt of a mineral acid, as in the case of cobalt(II) chloride (CoCl$_2$), cobalt(II) chloride hydrate (CoCl$_2$.6H$_2$O), cobalt(II) bromide (CoBr$_2$), and cobalt(II) nitrate hydrate (Co(NO$_3$)$_2$.6H$_2$O), etc., or as the salt of a suitable organic carboxylic acid, for example, cobalt(II) formate, cobalt(II) acetate, cobalt(II) propionate, cobalt naphthenate, cobalt acetylacetonate, etc. The cobalt may be added to the reaction zone as a carbonyl or hydrocarbonyl derivative. Here, suitable examples include dicobalt octacarbonyl (Co$_2$(CO)$_8$), cobalt hydrocarbonyl (HCo(CO)$_4$) and substituted carbonyl species such as the triphenylphospine cobalt tricarbonyl dimer, etc.

Preferred cobalt-containing compounds include oxides of cobalt, cobalt salts of a mineral acid, cobalt salts of organic carboxylic acids and cobalt carbonyl or hydrocarbonyl derivatives. Among these, particularly preferred are cobalt(III) acetylacetonate, cobalt(II) acetate, cobalt(II) propionate, and especially preferred is dicobalt octacarbonyl.

D. Quaternary Phosphonium Salt

As previously mentioned in the process of this invention, the reaction, when using catalyst components in solution, rather than on a fixed support, includes a quaternary phosphonium salt.

Quaternary phosphonium salts suitable for use in this invention have the formula:

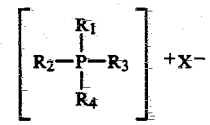

where R$_1$, R$_2$, R$_3$ and R$_4$ are organic radicals, particularly aryl or alkaryl radicals bonded to the phosphorous atom, and X is an anionic species. The organic radicals useful in this instance include those alkyl radicals having 1 to 20 carbon atoms in a branched or linear alkyl chain; they include the methyl, ethyl, n-butyl, iso-butyl, octyl, 2-ethylhexyl and dodecyl radicals. Tetraethylphosphonium bromide and tetrabutylphosphonium bromide are typical examples presently in commercial production. The corresponding phosphonium acetates, nitrates, chromates, tetrafluoroborates and halides, such as bromides or chlorides, are also satisfactory in this instance.

Equally useful are the phosphonium salts containing phosphorus bonded to a mixture of alkyl, aryl and alkaryl radicals. Said aryl and alkaryl radicals may each contain 6 to 20 carbon atoms. The aryl radical is most commonly phenyl. The alkaryl group may comprise phenyl substituted with one or more C$_1$–C$_{10}$ alkyl substituents, bonded to the phosphorus atom through the aryl function.

Illustrative examples of suitable quaternary phosphonium salts include tetrabutylphosphonium bromide, heptyltriphenylphosphonium bromide, tetrabutylphosphonium chloride, tetrabutylphosphonium nitrate, tetrabutylphosphonium chromate, tetrabutylphosphonium tetrafluoroborate, tetrabutylphosphonium acetate and methyltriphenylphosphonium bromide.

The preferred quaternary salts are generally the phosphonium salts containing alkaryl groups which may comprise, for example, phenyl substituted with one or more alkyl substituents. Methyltriphenylphosphonium salt works well and preferred salts include the bromide, chloride, acetate and chromate salts. Methyltriphenylphosphonium bromide is most preferred for the practice of this invention. Mixtures of these quaternary salts may also be employed if desired.

E. Acid

In the first embodiment of the process of this invention wherein acetic acid is produced by use of a soluble catalyst an inorganic acid is used in combination with a ruthenium compound, cobalt compound and a quaternary phosphonium salt.

The organic acids useful in this process are methanesulfonic and p-toluenesulfonic and trifluoromethanesulfonic acid, and NAFION ®. The inorganic acid must be sulfuric acid.

Preferred organic acids are methanesulfonic acid and NAFION ® as exemplified by Example I and X. An especially preferred organic acid is methanesulfonic acid.

In the second practice of the process of the instant invention for producing acetic acid on a solid carrier or support, an acid is used as a promoter in combination with supported 1% ruthenium on carbon catalyst. The acids useful in this process are trifluoromethane sulfonic acid. Generally, those acids applicable in the homogenous case above should be effective in the use of heterogeneous catalysts. Surprisingly, the heterogeneous acid NAFION ® physically mixed with the heterogeneous catalyst is also effective.

Preferred acids are sulfonic acids, containing sulfur as exemplified by NAFION ®, methane sulfonic acid and trifluoromethanesulfonic acid. NAFION ® is the trademark for a perfluorosulfonic acid membrane used in the manufacture of chlorine and caustic soda which is a chemically stable ion exchange resin.

F. Feedstock Composition

The preferred feedstocks for this carbonylation process are alcohols of 1 to 12 carbon atoms. Methanol is a particularly preferred feed for producing acetic acid selectively but where it is desirable to produce high proportions of carboxylic acid product, the liquid discharge may also include by-products or co-products which are recycled along with the aliphatic alcohol.

Ruthenium-catalyzed alcohol/ester carbonylation may also be conducted in the presence of one or more inert diluents. Preferably these diluents should have boiling points higher than that of the product acids. Suitable inert diluents that may aid in the desired carbonylation process include aromatic hydrocarbons of from 6 to 20 carbon atoms, higher-boiling organic carboxylic acids and the esters of the aforementioned acids in combination with the feedstocks undergoing carbonylation.

G. Catalyst Components

The quantity of ruthenium catalyst employed in the instant invention is not critical and may vary over a wide range. In general, the carbonylation process is desirably conducted in the presence of a catalytically effective quantity of the active ruthenium species which gives the desired acid products in reasonable yields. The reaction proceeds when employing concentrations of ruthenium in solution of between 0.05 wt % and 20 wt % or on a support of between 0.01 wt % and 10 wt %. This is the range normally employed, with the preferred range being 0.1 wt % to 5 wt %. Higher concentrations of ruthenium may be used to the extent of 20 wt %.

The quantity of cobalt-containing compound used in the catalyst of the first embodiment of the process is not critical and may vary over a wide range. The reaction proceeds when employing concentrations of cobalt in solution of between 0.01 wt % and 20 wt %. This range is normally employed, with the preferred range being 0.1 wt % to 5 wt %. High concentrations of cobalt may be used to the extent of 20 wt %.

The quantity of substituted quaternary phosphonium salt or base used in the first embodiment of the catalyst system to produce acetic acid may vary over a wide range also. The reaction proceeds when employing concentrations between 5 wt % and 50 wt %. The preferred range is between 15 wt % and 30 wt %. Higher concentrations may be used to the extent of 50 wt %.

The quantity of inorganic acid used in the fluid catalyst system of the first embodiment or as the promoter when a support is used may vary. In the first embodiment, using the soluble catalyst the reaction proceeds when employing concentrations between 1% and 30%. The preferred range is between 5% and 10%. Higher concentrations may be used to the extent of 30%.

When an inorganic acid is employed as a promoter, the reaction is improved when employing concentrations as low as 1% and the promoter is useful in amounts as high as 30%. The preferred range is between 5% and 10%.

H. Operation Temperature

The temperature range which can usefully be employed in these acid syntheses is a variable, dependent upon other experimental factors including the choice of alcohol reactant, the pressure, and the concentration and particular choice of catalyst, among other things. Again using ruthenium as the active metal, the range of operability is from about 30° to at least 400° C., when superatmospheric pressures of syngas are employed. A narrower range of 180°–350° C. represents the preferred temperature range when the major products are aliphatic carboxylic acids and their ester derivatives. Table I is evidence of how the narrower range is derived.

I. Pressure

Superatmospheric pressures of 500 psi or greater lead to substantial yields of desirable acetic acid by the process of this invention. A preferred operating range for solutions of ruthenium compound in combination with quaternary phosphonium salt and a cobalt compound is from 500 psi to 8000 psi, although pressures above 8000 psi also provide useful yields of desired acid. The preferred range is 3500–7500 psi. Table I is evidence of this preferred narrower range of operating pressures. The pressures referred to here represent the total pressure generated by all the reactants, although they are substantially due to the carbon monoxide fraction in these examples. The pressure range for the ruthenium on carbon is 500 to 8000 psi and preferred is 3000–4000 psi.

J. Gas Compositions

Insofar as can be determined, the best selectivities and yields of acetic acid can be obtained within a reasonable reaction period by using a substantially carbon monoxide gaseous atmosphere. In all syntheses, the amount of carbon monoxide present in the reaction mixture is a variable, but sufficient carbon monoxide should be present to satisfy the stoichiometry of Equation 1.

Particularly in continuous operations, but also in batch experiments, the carbon monoxide may also be used in conjunction with up to 50% by volume of one or more other gases. These other gases may include one or more inert gases such as nitrogen, argon, neon and the like, or they may include gases that may, or may not, undergo reaction under CO carbonylation conditions such as carbon dioxide, hydrogen, hydrocarbons such as methane, ethane, propane and the like, ethers such as dimethyl ether, methylethyl ether and diethyl ether, alkanols such as methanol and acid esters such as methyl acetate.

K. Product Distribution

As far as can be determined, without limiting the invention thereby, the ruthenium catalyst, one-step carbonylation process disclosed herein leads to the formation of two classes of primary products. The first class of primary products is carboxylic acids, preferably aliphatic carboxylic acids containing two or more carbon atoms. The second class of primary products are ester derivatives of these carboxylic acids. In the case where methanol is the alcoholic reactant the principal products are acetic acid and methyl acetate. Minor by-products detected in the liquid product fraction include small amounts of water, ethyl acetate and dimethyl ether. Carbon dioxide, methane and dimethyl ether may be detected in the off-gas together with unreacted carbon monoxide.

L. Identification Procedure

The products of carbonylation have been identified in this work by one or more of the following analytical procedures, viz, gas-liquid phase chromatography (glc), infrared (ir), mass spectrometry, nuclear magnetic resonance (nmr) and elemental analyses, or a combination of these techniques. Analyses have, for the most part, been by parts by weight; all temperatures are in degrees centigrade and all pressures in pounds per square inch gauge (psi).

M. Mode of Operation

The process of this invention can be conducted in a batch, semi-continuous or continuous fashion. The ruthenium compound, quaternary salt or base, cobalt compound and inorganic acid catalyst may be introduced into the reaction zone batchwise, or may be continuously or intermittently introduced into such a zone during the course of the synthesis reaction. Operating conditions can be adjusted to optimize the formation of the desired acid product, and said material may be recovered by methods well known in the art, such as distillation, fractionation, extraction and the like.

The ruthenium on carbon catalyst may be employed as a fixed or fluid bed; the reactor may consist of a series of catalyst beds or the catalyst may be placed in tubes with a heat exchange medium around the tubes. So as to provide certain operating advantages, the metal content of the catalyst can be varied through the reactor bed, and the reactants may be passed up-flow or down-flow through the reactor.

Generally, operating conditions can be adjusted to optimize the formation of any desired acid product, and said materials may be recovered by methods well known in the art, such as distillation, fractionation, extraction and the like. By-product esters, methyl and ethyl acetate, may then be recycled to the reaction zone, if desired, and additional acid and/or anhydride and ester products generated by CO carbonylation.

Having described the inventive process in general terms, the following examples are submitted to supply specific and illustrative embodiments.

EXAMPLE I

Example I illustrates the use of the combination $RuO_2/CH_3Ph_3PBr/Co_2(CO)_8$ and an organic acid catalyst found to be very effective in catalyzing methanol carbonylation into acetic acid.

A glass liner was charged with ruthenium oxide hydrate (0.19 g, 1.0 mm), methyltriphenylphosphonium bromide (4.25 g, 10 mm), dicobalt octacarbonyl (0.17 g 0.5 mmole) 8.0 g methanol and 0.5 g methanesulfonic acid. The glass liner was charged in a stainless steel reactor and purged of air, pressured to 4000 psi of carbon monoxide, then heated to 220° C. The pressure reached to 6550 psi, then dropped to 6100 psi during the reaction procedures. After 18 hours, the reaction was stopped and the reactor was allowed to cool to room temperature. The off-gas sample was taken by a gas-bomb and excess gas vented from the reactor following which 15.5 g of brown product was recovered.

Analysis of the liquid product by GLC showed the following product composition:
0% methanol
82.5% acetic acid
8% methyl acetate
9% ethyl acetate.

The water content as determined by Karl-Fischer titration was 0.19%. A typical off-gas sample showed the presence of:
84.7% carbon monoxide
6.6% hydrogen
0.6% methane
6% carbon dioxide.

It is noted that the yield of acetic acid is >82%, using a catalyst system which has the distinct advantage of being iodine free. Another unique characteristic of this catalyst system is its capacity for water-gas-shift-reaction which is evidenced by the appearance of $H_2$ in the off-gas sample and also the formation of ethyl acetate in the ligand products. Water was produced "inside" by the esterification of methanol and acetic acid among these byproducts. Methyl acetate can be recycled and ethyl acetate can be hydrolyzed into ethanol and acetic and therefore the overall reaction is to produce acetic acid and ethanol, a useful byproduct.

EXAMPLES II Through XI

Examples II through X in Table I were carried out using the same procedure as was used in Example I. It is noted that there is some variation in molar ratios, concentration and choice of sulfur-containing acid promoter, and variation in pressure used.

TABLE I

Acetic Acid Synthesis Via Methanol Carbonylation[1]

| Example | Catalyst (mmole used) | Promoter Added | Reaction[2] Pressure | Methanol Conversion (%) | Liquid wt. gain | product selectivities % | | |
|---------|----------------------|----------------|----------------------|-------------------------|-----------------|------|------|------|
| | | | | | | Acetic Acid | Methyl Acetate | Ethyl Acetate |
| II | $RuO_2/CH_3Ph_3Br/Co_2(CO)_8$ (1:10:0.5) | $CH_3SO_3H$ (1.0 g) | 4775–4300 psi | 100 | 1.5 g | 57 | 33 | 9 |

TABLE I-continued

Acetic Acid Synthesis Via Menthanol Carbonylation[1]

| Example | Catalyst (mmole used) | Promoter Added | Reaction[2] Pressure | Methanol Conversion (%) | Liquid wt. gain | product selectivities % | | |
|---|---|---|---|---|---|---|---|---|
| | | | | | | Acetic Acid | Methyl Acetate | Ethyl Acetate |
| III | RuO₂/CH₃Ph₃Br/Co₂(CO)₈ (1:10:0.5) | CH₃SO₃H (1.0 g) | 6450–5500 psi | " | 3.85 | 69 | 16 | 14 |
| IV | RuO₂/CH₃Ph₃Br/Co₂(CO)₈ (1:10:0.5) | CH₃SO₃H (2.0 g) | 7450–6500 psi | " | 1.05 | 33 | 44 | 24 |
| V | RuO₂/CH₃Ph₃Br/Co₂(CO)₈ (1:10:2) | CH₃SO₃H (0.5 g) | 4375–3900 psi | " | 1.40 | 65 | 11 | 17 |
| VI | RuO₂/C₇H₁₅Ph₃PBr/CO₂(CO)₈ (1:10:0.25) | CH₃SO₃H (0.5 g) | 6550 psi | " | 4.05 | 72 | 13 | 13 |
| VII | RuO₂/C₇H₁₅Ph₃PBr/CO₂(CO)₈ (1:10:1) | P—toluene-Sulfonic Acid (2.1 g) | 5075–3880 psi | " | 3.60 | 50 | 27 | 22 |
| VIII | RuO₂/C₇H₁₅Ph₃PBr/CO₂(CO)₈ (1:10:1) | CF₃SO₃H (1.0 g) | 5575–3880 psi | " | 1.45 | 52 | 16 | 30 |
| IX | RuO₂/C₇H₁₅Ph₃PBr/CO₂(CO)₈ (1:10:0.5) | H₂SO₄ (0.5 g) | 5800 psi | " | 1.3 | 75 | 3 | 18 |
| X | RuO₂/C₇H₁₅Ph₃PBr/CO₂(CO)₈ (1:10:0.5) | NAFION ® (0.5 g) | 6200–5200 psi | " | 2.15 | 64 | 3 | 25 |
| XI | RuO₂/C₇H₁₅Ph₃PBr/CO₂(CO)₈ (1:10:0.5) | NAFION ® (0.5 g) | 4500–4025 psi 200° C. | " | 2.5 | 56 | 19 | 20 |

[1] 8.0 g MEOH was used
[2] pure CO was charged and the reacting conditions of 220° C. and 18 hours were used

COMPARATIVE EXAMPLE XII

Example XII and Examples XIII through XV which follow illustrate the process by which acetic acid is produced by carbonylation of methanol over a 1% ruthenium on carbon catalyst in the presence of a sulfur-containing acid promoter where the catalyst contains no iodine.

In Example XII methanol and 25% excess carbon monoxide was charged to a 25 cc continuous reactor at 350° C. and 3000 psig. The reactor contained 25 cc of a mixture obtained by dispersing 4 cc NAFION ® 511 in 23 cc of a 1% ruthenium-on-carbon catalyst. The methanol was charged at a LHSV of 0–25 hr.$^{-1}$. The effluent was collected and analyzed by gas chromatography. Methanol conversion was 73.2% with selectivities to water, methyl acetate and acetic acid of 59.7, 36 and 2.4 respectively.

This illustrates a heterogenous ruthenium catalyst effective for methanol carbonylation into acetic acid and methyl acetate, using a strong acid promoter instead of iodide.

COMPARATIVE EXAMPLE XIII

Example XIII illustrates that the use of methane sulfonic acid as a promoter with the supported catalyst results in low productivity for acetic acid as did NAFION ® in Example XII.

In Example XIII methanol containing 1 wt % MeSO₃H and 108 ppm ruthenium was fed to a 25 cc continuous reactor at 350° C. and 3000 psig along with a 25% excess of carbon monoxide. The reactor was filled with 1% ruthenium on carbon catalyst. The methanol solution was charged at a LHSV of 0.25 hr.$^{-1}$. Methanol conversion was 76.6% and selectivities to H₂O, methyl acetate and acetic acid were 81%, 6.9% and 11.1% respectively. Copious amounts of water are formed and acetic acid productivity is low.

EXAMPLE XIV

Example XIV illustrates the effectiveness of the process of this invention using trifluoromethane sulfonic (CF₃SO₃H) as a promoter. In this example methanol containing 1 wt % CF₃SO₃H and 25% excess carbon monoxide was charged to a 25 cc continuous reactor at 275° C. and 3000 psig. The reactor was filled with 1% ruthenium-on-carbon. The methanol solution was charged at a LHSV of 0.25 hr.$^{-1}$. Methanol conversion was >99% and the selectivity to water, methyl acetate and acetic acid was 8.1%, 10.3% and 79.1%, respectively.

EXAMPLE XV

In a continuation of Example XIV the temperature in the reactor was raised to 350° C. Methanol conversion was 100% and selectivity to H₂O, MeOAc and HOAc were 11.9%, 2.6% and 84.9% respectively; however, the trifluorosulfonic acid catalyst decomposed liberating the sulfur dioxide.

What is claimed is:

1. A process for the preparation of acetic acid by carbonylation of methanol which comprises
   (a) contacting methanol and carbon monoxide in the presence of an iodide-free soluble catalyst system consisting essentially of a ruthenium-containing compound, a quaternary phosphonium salt, a cobalt-containing compound and an inorganic or organic acid selected from the group consisting of methane-sulfonic acid, trifluoromethanesulfonic acid, sulfuric acid and NAFION ®, or an iodide-free solid support catalyst system consisting essentially of a ruthenium-containing compound on an inert support and trifluoromethane sulfonic acid,
   (b) heating the resulting reaction mixture to a temperature of at least 150° C. and a pressure of about 500 psi to 8000 psi until substantial formation of the desired acid and
   (c) isolating said acetic acid contained therein.

* * * * *